United States Patent [19]

Ranford et al.

[11] Patent Number: 5,156,599
[45] Date of Patent: Oct. 20, 1992

[54] SYRINGE AND SLIDING LOCKING NEEDLE SHIELD

[75] Inventors: Alan B. Ranford, Creve Coeur; Daniel A. Talonn, University City, both of Mo.

[73] Assignee: Sherwood Medical Company, St. Louis, Mo.

[21] Appl. No.: 364,939

[22] Filed: Jun. 9, 1989

Related U.S. Application Data

[63] Continuation-in-part of Ser. No. 212,528, Jun. 28, 1988, Pat. No. 5,053,018.

[51] Int. Cl.⁵ .............................................. A61M 5/32
[52] U.S. Cl. ........................................ 604/198; 604/192; 604/263; 128/919
[58] Field of Search ......................... 604/192, 195-198, 604/263, 110; 128/919

[56] References Cited

U.S. PATENT DOCUMENTS

| | | |
|---|---|---|
| 2,571,653 | 10/1951 | Bastien . |
| 3,780,734 | 12/1973 | Wulff . |
| 3,890,071 | 6/1975 | Leeson et al. . |
| 4,170,993 | 10/1979 | Alvarez . |
| 4,356,822 | 11/1982 | Winstead-Hall . |
| 4,425,129 | 1/1984 | Sampson et al. . |
| 4,573,976 | 3/1986 | Sampson et al. . |
| 4,631,057 | 12/1986 | Mitchell . |
| 4,643,199 | 2/1987 | Jennings, Jr. et al. ............ 128/763 |
| 4,643,200 | 2/1987 | Jennings, Jr. . |
| 4,650,468 | 3/1987 | Jennings, Jr. . |
| 4,655,751 | 4/1987 | Harbaugh ............ 604/198 |
| 4,666,435 | 5/1987 | Braginetz . |
| 4,681,567 | 7/1987 | Masters et al. . |
| 4,693,708 | 9/1987 | Wanderer et al. . |
| 4,695,274 | 9/1987 | Fox ............ 604/198 |
| 4,702,738 | 10/1987 | Spencer ............ 604/198 |
| 4,723,943 | 2/1988 | Spencer ............ 604/198 |
| 4,737,144 | 4/1988 | Choksi . |
| 4,738,663 | 4/1988 | Bogan ............ 604/198 |
| 4,743,233 | 5/1988 | Schneider . |
| 4,840,185 | 6/1989 | Hernandez ............ 604/198 |
| 4,842,587 | 6/1989 | Poncy . |
| 4,871,355 | 10/1989 | Kikkawa ............ 604/198 |
| 4,874,383 | 10/1989 | McNaughton ............ 604/198 |
| 4,892,523 | 1/1990 | Haber et al. ............ 604/198 |
| 4,894,055 | 1/1990 | Sudnak ............ 604/198 |
| 4,900,311 | 2/1990 | Stern et al. ............ 604/198 |
| 4,908,023 | 3/1990 | Yuen ............ 604/198 |
| 4,917,673 | 4/1990 | Coplin ............ 604/198 |
| 4,923,445 | 5/1990 | Ryan ............ 604/195 |
| 4,923,447 | 5/1990 | Morgan ............ 604/198 |
| 4,932,940 | 6/1990 | Walker et al. ............ 604/110 |
| 4,935,016 | 6/1990 | Deleo ............ 604/198 |
| 4,976,702 | 12/1990 | Andrew et al. ............ 604/198 |
| 4,994,045 | 2/1991 | Ranford ............ 604/198 |
| 4,998,924 | 3/1991 | Ranford ............ 604/198 |
| 5,011,479 | 4/1991 | Le et al. ............ 604/198 |
| 5,019,049 | 5/1991 | Haining ............ 604/165 |
| 5,019,051 | 5/1991 | Hake ............ 604/198 |
| 5,024,616 | 6/1991 | Ogle ............ 604/192 |
| 5,029,660 | 6/1991 | McNaughton ............ 604/190 |
| 5,030,209 | 7/1991 | Wanderer et al. ............ 604/198 |
| 5,045,066 | 9/1991 | Scheuble et al. ............ 604/198 |

FOREIGN PATENT DOCUMENTS

| | | |
|---|---|---|
| 216460 | 4/1987 | European Pat. Off. . |
| 2240987 | 10/1987 | European Pat. Off. . |
| 250104 | 12/1987 | European Pat. Off. . |
| 2252644 | 1/1988 | European Pat. Off. . |
| 2833804 | 3/1979 | Fed. Rep. of Germany . |
| 8606355 | 10/1986 | Fed. Rep. of Germany . |
| 3609516 | 6/1987 | Fed. Rep. of Germany . |

*Primary Examiner*—C. Fred Rosenbaum
*Assistant Examiner*—Mark O. Polutta
*Attorney, Agent, or Firm*—Andrew J. Beck; Montgomery W. Smith; Richard D. Allison

[57] ABSTRACT

A safety syringe having a protective barrel which is movable between a retracted position wherein the needle is exposed and a locked extended position wherein the needle is protected. A collar is attached to the distal end of the sleeve to selectively engage a key on the shield in the retracted and extended positions. The locking mechanism preferably includes a series of ramps and slots which engage portions of the shield to retain the shield in the retracted and extended positions. The shield slides longitudinally between the retracted and extended positions and may be rotated about the barrel of the syringe to irreversibly lock the shield in the extended position.

11 Claims, 6 Drawing Sheets

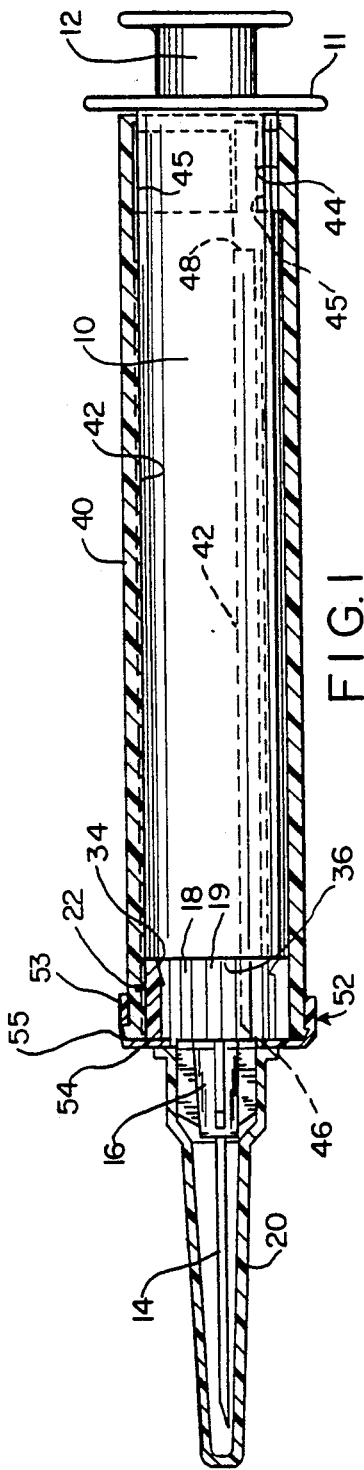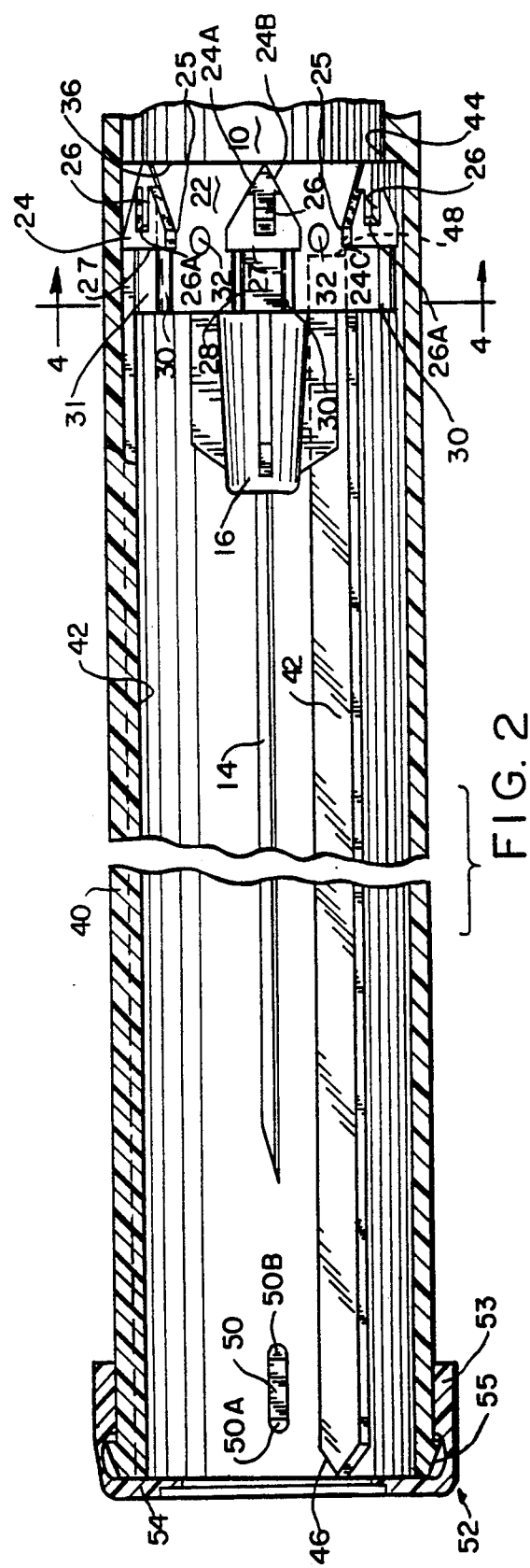

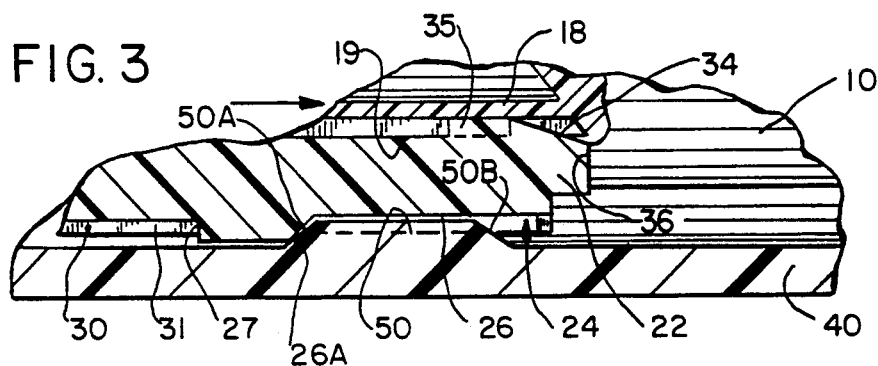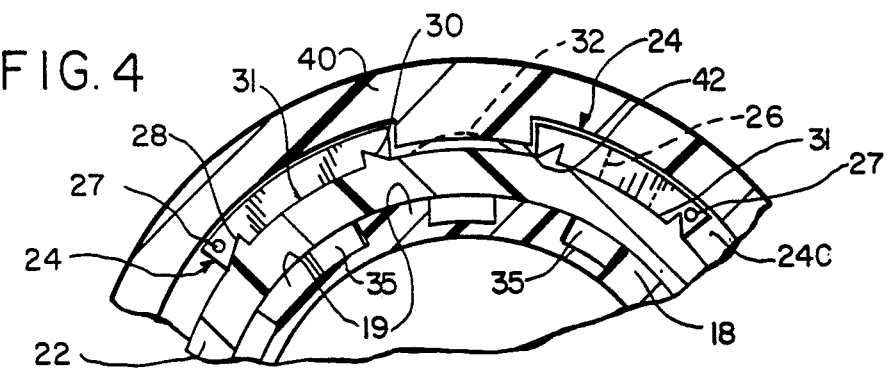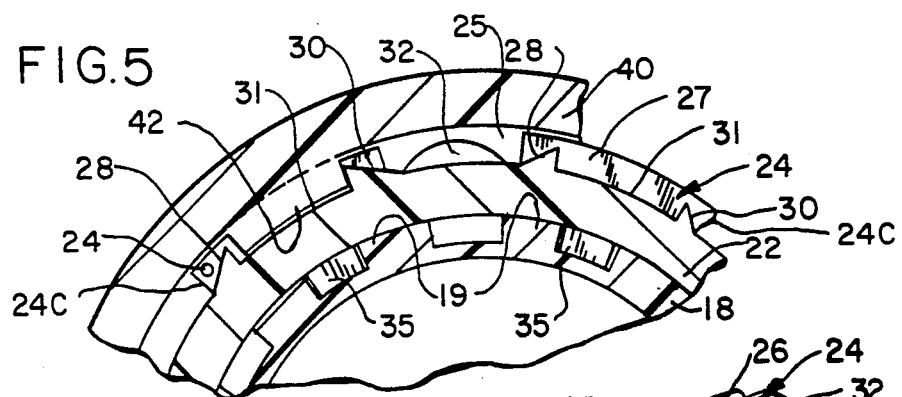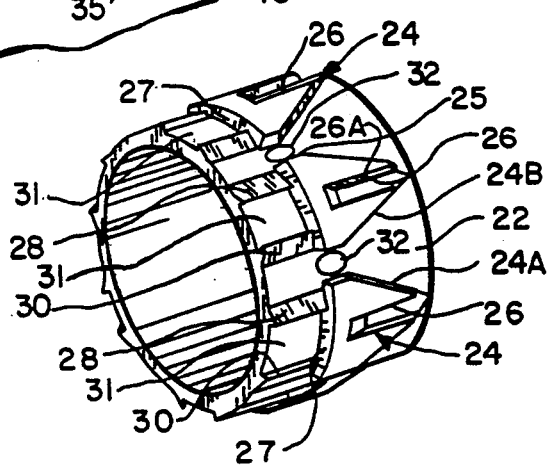

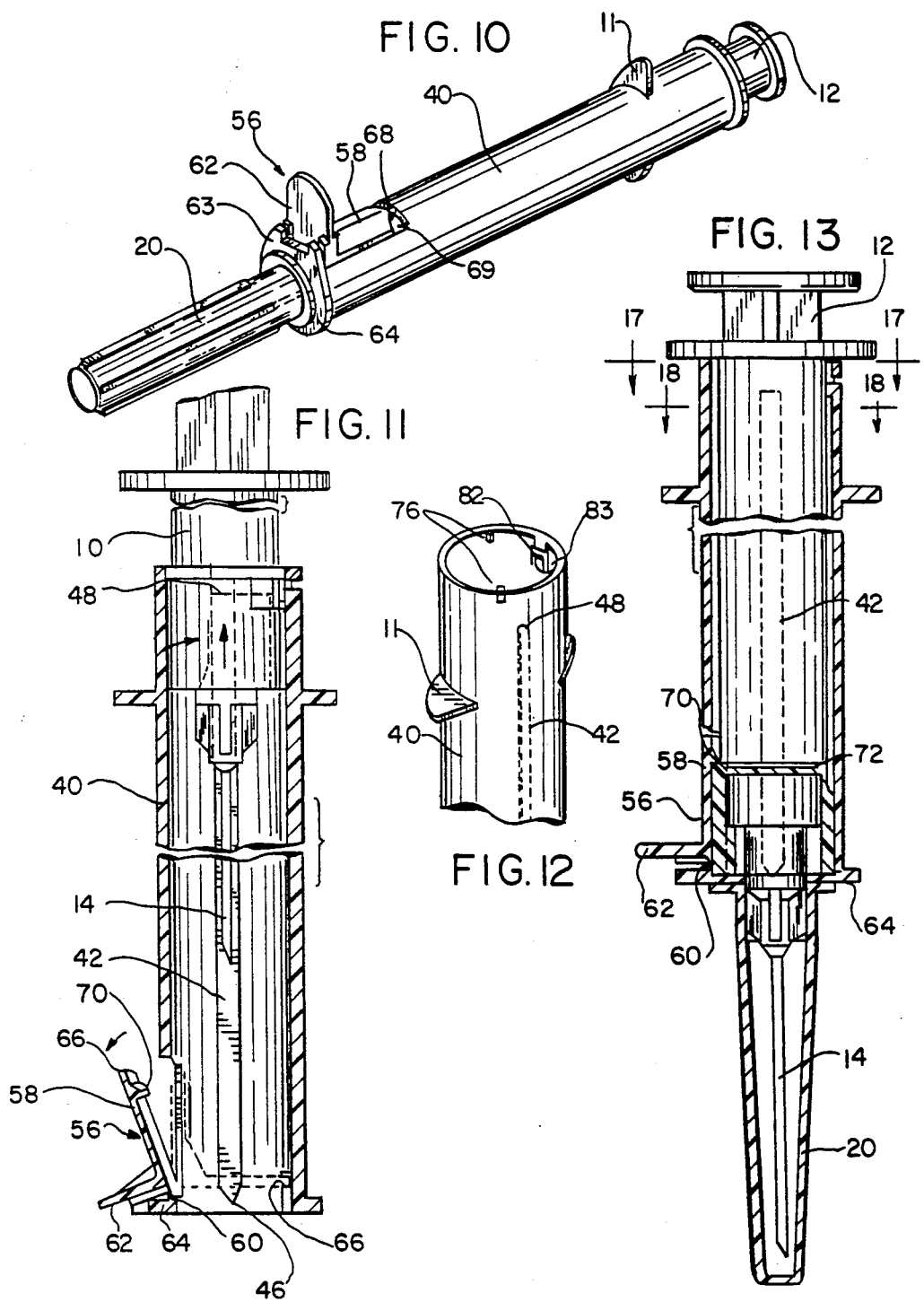

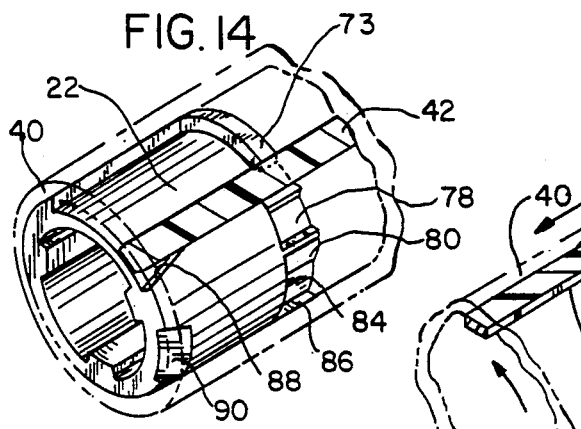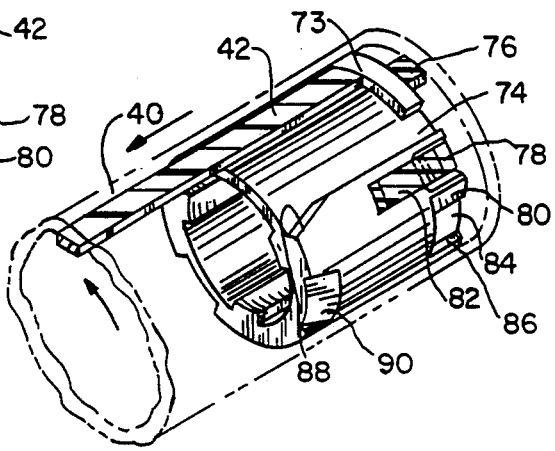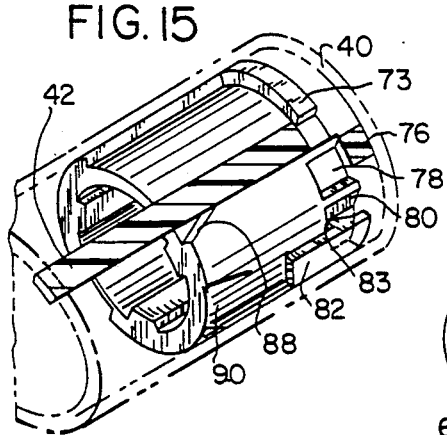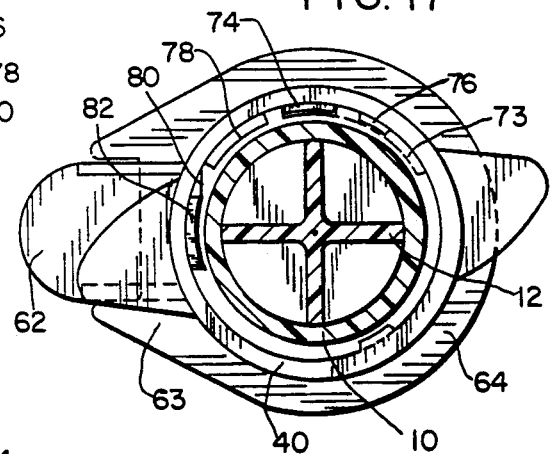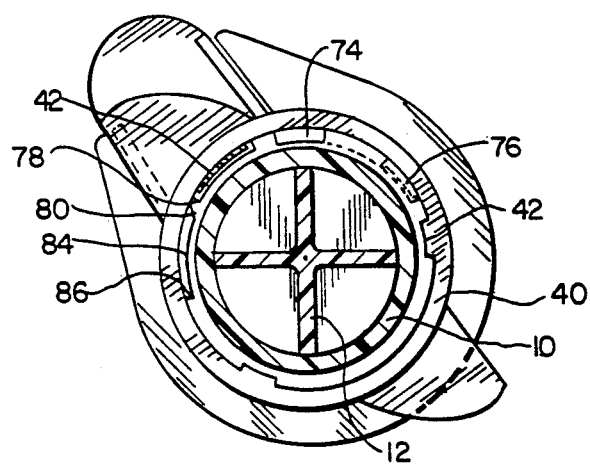

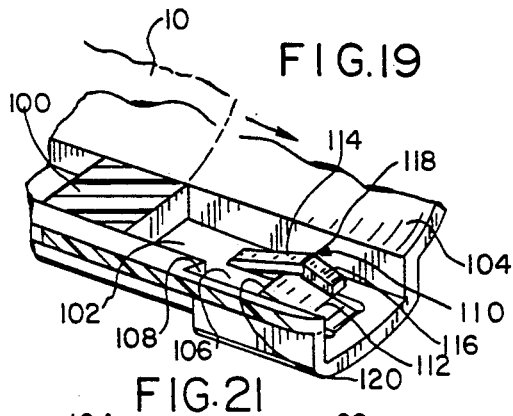
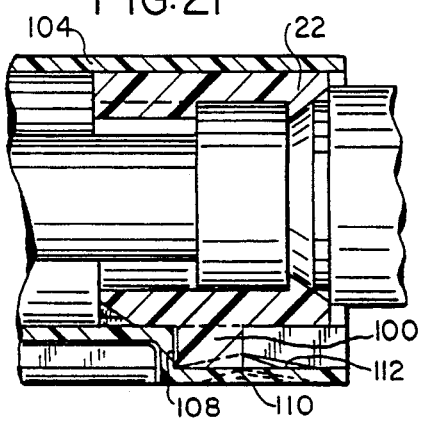
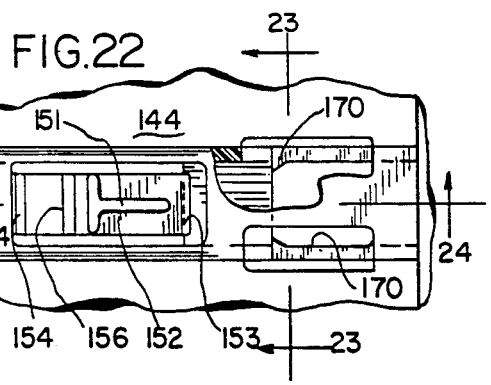
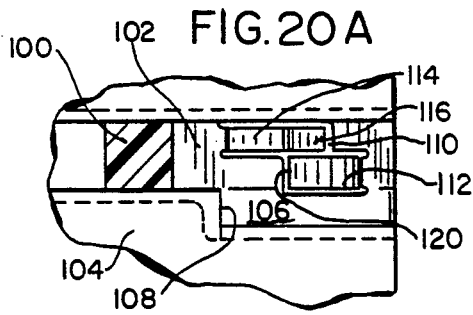
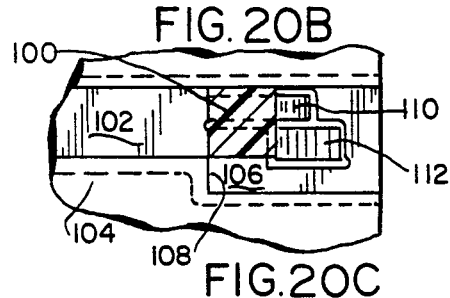
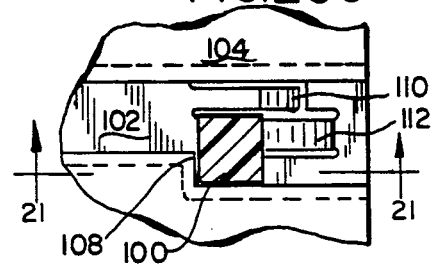
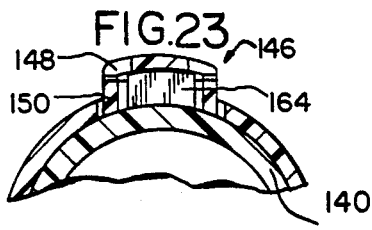
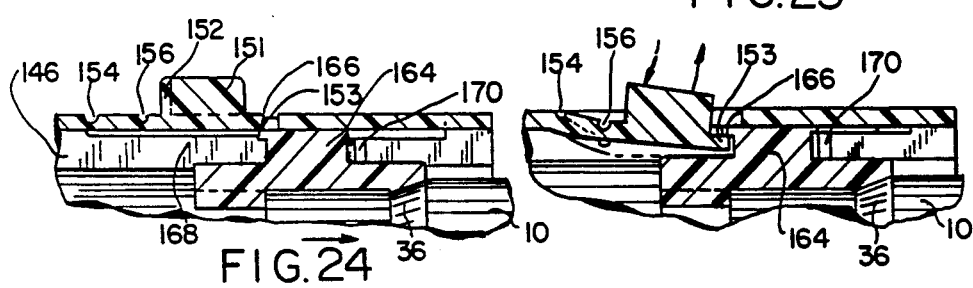
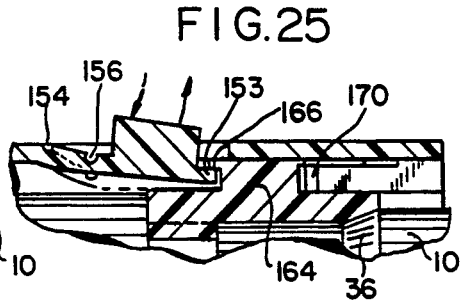

SYRINGE AND SLIDING LOCKING NEEDLE SHIELD

RELATED U.S. PATENT INFORMATION

This application is a continuation in part of a copending application filed June 28, 1988, having Ser. No. 212,528 now U.S. Pat. No. 5,053,018.

FIELD OF THE INVENTION

This invention relates to syringes and, in particular, to a syringe having a retractable needle guard primarily for the purpose of preventing accidental needle sticks.

BACKGROUND OF THE INVENTION

Most syringes used today for medical or laboratory purposes are sold as disposable items intended to be used only once. Disposal of such syringes poses a potential safety hazard for the individuals who use the syringes as well as for those who dispose of them. With the onset of AIDS, the concern for infection due to accidental needle sticks from used syringes has increased and a number of different devices have been proposed to minimize the possibility of spreading infectious disease due to accidents of this type.

One approach to this problem is to provide a retractable shield which, after the syringe has been used, can be pulled to an extended position where it covers the needle, making it difficult for an individual to accidentally contact the needle. A common feature of such constructions is that when the shield is pulled to its extended position, it is locked so that it cannot be retracted (thus exposing the needle) except by the application of extraordinary force to the shield.

A number of such constructions have been proposed to satisfy the general requirement that the needle be permanently covered after the syringe has been used. Some of these constructions involve twist-to-lock mechanisms and, in others, locking occurs automatically when the shield is fully extended. These known devices satisfy many of the functional requirements of a needle shield but require, in many cases, modification of the standard syringe construction. This is highly undesirable for many syringe manufacturers because of the sizable investment they may have already made in their existing molding equipment for producing the syringes.

Moreover, certain operational problems arise when a shield is incorporated into a syringe. For example, since the shield, when it is retracted, essentially covers the barrel of the syringe, it is desirable to be able to insert and remove a needle while holding onto the shield alone. This involves twisting and pushing (or pulling) the needle to place it on (or remove it from) the luer and can be awkward with some known constructions.

Further, constructions have been proposed which include an opening or slot in the side of the shield. This is undesirable because the needle can extend through the opening if the shield is deflected in the extended position.

Those devices which lock in response to axial movement to the extended position, (i.e., without any rotation) also have certain inherent drawbacks. The major drawback to this type of device is that the incidence of unintentional and irreversible locking is greater with such devices than with those devices which require rotation to lock.

Other proposed devices have included open ended shields which may not block access to the needle point by small fingers.

Accordingly, it is an object of this invention to provide a protective shield of the type described which can be added at minimal expense to standard syringes.

Another object of the invention is to provide a relatively inexpensive protective shield which satisfies the functional requirements of a needle shield and includes none of the drawbacks mentioned above.

Another object is to provide an extendable needle shield for a syringe which performs all of the necessary functions of such a shield and which is particularly well suited to an automated process of manufacture.

A further object of the invention is to provide an extendable needle shield for a standard syringe which is improved both from the points of view of functional utility and cost of manufacture.

A still further object is to provide an inexpensive method of assembling a protective shield and syringe.

SUMMARY OF THE INVENTION

In accordance with the invention, a needle shield is mounted coaxially on a syringe barrel. The shield is movable over the barrel between a retracted position in which the needle is exposed and an extended position in which it surrounds and protects the needle. In one embodiment, the shield has an opening along its side wall near its distal end. A trigger member is positioned within this side wall opening and pivotally connected to the shield by a flexible hinge. The trigger member is movable from an outward position to an inward position and is shaped so that when it is in the inward position it substantially covers the distal end opening. A locking means is provided for locking the trigger member in the inward position. The locking means is provided for selectively covering the side wall opening so that the needle becomes completely surrounded and protected.

Other benefits and embodiments of the present invention are set forth below in the detailed description which follows:

IN THE DRAWINGS

FIG. 1 is a side elevational view, partly in section, showing a needle shield and collar in accordance with a preferred embodiment of the invention secured to a conventional syringe with the shield in its retracted position;

FIG. 2 is an enlarged sectional view with the shield in cross-section in its extended position;

FIG. 3 is a further enlarged partial side sectional view showing details of the collar and shield;

FIG. 4 is a sectional view along the line 4-4 of FIG. 2 with the shield pulled to its extended position but before rotation;

FIG. 5 is a sectional view along the line 4-4 of FIG. 2 showing the shield rotated into its locked position;

FIG. 6 is a perspective view of a preferred embodiment of the collar;

FIG. 10 is a perspective view showing a needle shield and a collar according to a second embodiment of the invention secured to a conventional syringe with the shield in its retracted position;

FIG. 11 is a sectional view of the shield according to a further embodiment of the invention with the shield in its extended position;

FIG. 12 is a partial perspective view of the shield of the embodiment illustrated in FIG. 11;

FIG. 13 is a side view, partly in section, showing the needle shield and collar according to the embodiment illustrated in FIG. 11 with the shield in its retracted position;

FIG. 14 is a perspective view showing the details of the collar of the embodiment illustrated in FIG. 11, with part of a shield, shown in phantom, in its retracted position and without the locking tab;

FIG. 15 is a perspective view of the collar according to the embodiment illustrated in FIG. 11 with part of the shield, shown in phantom in its extended, but unlocked, position;

FIG. 16 is a perspective view of the collar according to the embodiment illustrated in FIG. 11 showing part of the shield (in phantom), in its extended and locked position;

FIG. 17 is a sectional view of the embodiment illustrated in FIG. 11 taken generally along line 17—17 of FIG. 13 with the shield pulled to its extended position but before rotation in accordance with the third embodiment;

FIG. 18 is a sectional view of the embodiment illustrated in FIG. 11 taken generally along the line 18—18 of FIG. 13 showing the shield rotated into its locked position in accordance with the third embodiment;

FIG. 19 is an enlarged partial perspective sectional view showing the details of a locking mechanism and a shield according to a further embodiment of the invention;

FIGS. 20a, 20b and 20c are sectional views of the shield according to a further embodiment of the invention illustrated in FIG. 19 showing the sequence for locking the shield in its extended position;

FIG. 21 is an enlarged partial side sectional view along the line 21—21 of FIG. 20c showing the shield in its locked position according to the embodiment of the invention illustrated in FIG. 19;

FIG. 22 is an enlarged partial top sectional view showing the details of a locking mechanism of a shield according to a further embodiment of the invention;

FIG. 23 is a sectional view taken generally along the line 23—23 of FIG. 22;

Figure 7:
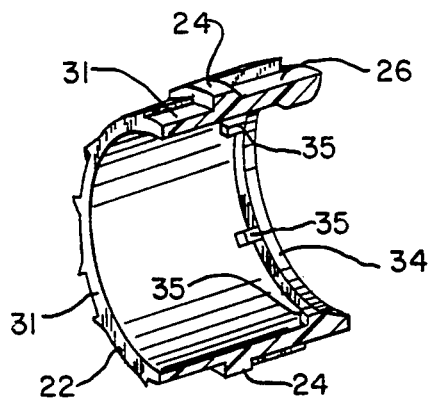
FIG. 7 is a perspective view of an alternative embodiment of the collar.

FIG. 24 is an enlarged partial side sectional view showing the details of the locking mechanism and a collar according to the embodiment of the invention illustrated in FIG. 22 with the shield in its extended but unlocked position; and FIG. 25 is an enlarged partial side sectional view showing the details of the locking mechanism and the collar according to the embodiment of the invention illustrated in FIG. 22 with the shield in its extended and locked position.

DETAILED DESCRIPTION OF THE INVENTION

In its preferred embodiment, the invention is intended to be used in conjunction with a conventional syringe; however, a protective shield in accordance with the invention may be modified for use with nearly any medical or laboratory device having a needle, such as a blood collection tube holder with a double ended needle without departing from the contemplated scope of the present invention. Accordingly, as used herein, the term "syringe" is intended to include any medical or scientific device including a needle wherein it is desired to protect a user from accidental needle sticks.

In describing the invention, the "distal end" or "forward end" of a part refers to the end of the part closest to the needle point. The "proximal end" of a part refers to the end of the part furthest from the needle point.

FIGS. 1-6 show a conventional syringe comprising a tubular barrel 10 having a finger flange 11, a plunger 12 slidable within the barrel 10, and a needle assembly through which the contents of the barrel are dispensed when the plunger 12 is depressed. The barrel 10 may be tapered very slightly (not shown) from a larger diameter proximal end to a smaller diameter distal end for primarily molding purposes. The needle assembly comprises a needle 14 and a hub 16 at the proximal end of the needle. As is standard, a conically shaped luer tip 17 and luer lock skirt 18 are integrally formed at the distal end of the barrel 10 with the luer lock skirt 18 encircling the luer tip 17. The interior surface of the luer lock skirt 18 may include an internal thread 18A adapted to threadably engage complementary locking ears 16A on the needle hub 16. The exterior surface of luer lock skirt 18 may include a multiplicity of ribs 19 parallel to the central axis of the barrel 10.

A needle sheath 20 covers the needle 14 as a protective device. The needle sheath 20 frictionally engages the hub 16 and can be used to disconnect the needle assembly from the luer lock skirt 18 in a conventional fashion.

The construction as so far described is that of a standard disposable syringe and forms no part of the invention.

The collar employed in accordance with the preferred embodiment of the invention is shown generally at 22 (FIGS. 2 and 6). As mentioned above, although collar 22 is shown as a separate piece made of differing materials, it is anticipated that the collar (or its functional equivalent) may be integrally formed as a part of the barrel 10 without substantial modification of the present invention. In this embodiment, the collar 22 includes six equally spaced and integrally formed identical triangular protrusions 24, with the apex of each protrusion extending away from the needle. Keyways 25 are formed between each adjacent pair of protrusions 24.

The triangular protrusions 24 each include angled surfaces 24A and 24B, side surfaces 25C, a slot 26 and a stop surface 27 which is generally circumferential and functions as a stop for the keys as further described below. The slot 26 includes an inwardly sloped distal surface 26A. It is not absolutely necessary that the protrusions 24 be triangular in shape and it is anticipated that other configurations may be used to guide the keys into the keyways during the assembly process as described below. The slot 26 is formed in protrusion 24 for retaining the detent 50 therein when the shield 40 is in the retracted position, as explained below. At the distal end of each protrusion 24, two walls 28 and 30 extend toward the needle. A rectangular locking slot 31 is formed between each pair of walls 28 and 30, which are ramp shaped in cross section as shown most clearly in FIGS. 4 and 5. As shown in FIGS. 3, 4 and 5, the surface of locking slot 31 is slightly elevated relative to the level of the keyways, i.e., the barrel diameter at the locking slots 31 is slightly greater than the barrel diameter at the keyways. The slight increase in the collar diameter at the locking slots removes some of the slack between the needle shield (described below) and the collar 22 resulting from the slight lengthwise taper of the barrel 10 in the preferred embodiment. This prevents or at least minimizes wobble or play of the shield when it is locked in the extended position. A spherical detent 32 is positioned between each pair of triangular protrusions 24 with the distal edge of the detents 32 lying just in front of the bases of triangular projections 24.

As shown most clearly in FIG. 3, the proximal end of collar 22 includes a peripheral rigid internal tooth 34 adapted to engage the ribs 19 in the luer lock skirt 18 and retain the collar 22 on the syringe. Collar 22 is molded of a rigid plastic material such as polycarbonate resin so that when the collar is pushed over the luer lock skirt 18, the angled surface of the rigid tooth 34 allows the tooth to move over the ribs 19 until the proximal end of the collar is seated adjacent to the distal end of the barrel with the rigid tooth 34 deforming the ribs 19 of the luer lock skirt 18 to permanently retain the collar in place on the syringe barrel 10. As an alternative, a circumferential groove may be formed in the outer surface of the luer lock skirt 18 to receive the peripheral tooth 34 of the collar 22 therein. This is unnecessary in the preferred embodiment in which the yieldable ribs 19 cold flow into the configuration shown in FIG. 3 but may be desirable in the case of syringes which do not include ribs molded on the exterior surface of the luer lock skirt. Instead of mechanically interlocking the collar 22 and barrel 10, other fastening means such as ultrasonic welding or adhesives may be used within the scope of the invention, although such techniques are generally disadvantageous because of the additional steps involved and other problems which may arise with the preferred assembly techniques. The diameter of collar 22 as measured in the area of the keyways 25 is greater than the outer diameter of the syringe barrel 10 adjacent to the collar 22.

Figure 8:
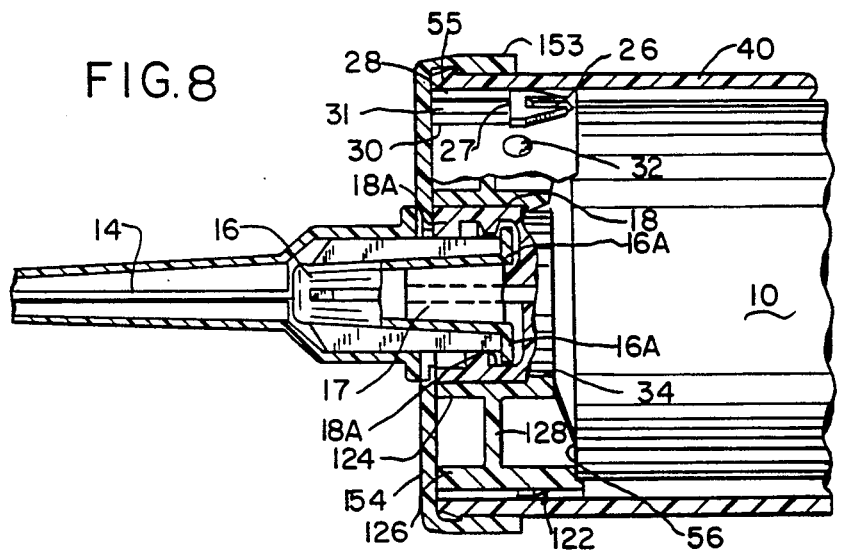
FIG. 8 is a top sectional view showing the shield in its locked position with the shield shown in FIG. 7.

The rigid tooth 34 will bite sufficiently into the outer surface of the luer skirt 18 to prevent axial movement of collar 22 but in some cases slight rotation of the collar may occur. To prevent this, the tooth 34 may be formed with gaps (not shown) so that not all of the ribs 19 on the outside of the luer lock skirt 18 will be deformed. The non-deformed ribs 19 will fall into the gaps of the tooth 34 resist rotation of the collar 22 relative to barrel 10. Alternatively, as shown in FIGS. 7 and 8, the inner surface of collar 22 may be provided with lugs 35 molded on the inside of the collar and adapted to fit between the ribs 19 on the outside of the luer lock skirt 18 to prevent any rotational movement with the meshed ribs 19.

The needle shield 40 comprises an elongated plastic cylinder (e.g., made of polypropylene) having three keys 42 integrally formed on its interior surface. An end rim 44 is formed at the proximal end of shield 40. As shown in FIG. 2, the end rim 44 is adapted to abut against the proximal end of collar 22 to limit the distal movement of the shield 40. Each of the keys 42 includes a distal triangular point 46 and extends from the distal end of the shield to a location just short of the distal point of the triangular protrusions 24 on collar 22 when the shield is in the extended position as shown in FIG. 2. The end rim 44 includes three cutout sections 45 which align with each of the keys 42. The cutout sections 45 facilitate the process for molding keys 42 but serve no functional purpose after the device has been assembled. At their proximal ends, the keys 42 terminate in flat end surfaces 48. With the three keys 42 in the keyways 25 in the retracted position (FIG. 1), rotational movement of the shield 40 is prevented by contact between the edges of keys 42 against the side surfaces 24C of protrusions 24; therefore, torque can be applied to the needle while holding shield 40 to thread (or unthread) needles onto (or from) the syringe without having to grasp the barrel 10. This cannot be done with constructions in which a shield rotates freely with respect to the syringe.

Three detents 50 are also formed on the inner surface of the shield 40 toward its distal end. These detents 50 may be equally spaced and are adapted to be received within the slots 26 in the triangular protrusions 24 to releasably retain the shield 40 in its retracted position (FIG. 1). In the preferred embodiment, as shown in the drawings, the detents 50 are preferably spaced approximately thirty degrees from an adjacent key 42. Each of the detents 50 includes a sloped distal surface 50A and a proximal surface 50B more gradually sloped than distal surface 50A.

In the retracted position, the distal end of shield 40 terminates at the same point as the distal end of collar 22. An end cap 52 (see FIG. 2) is placed on the distal end of the shield 40. Cap 52 is molded from a resilient plastic material (such as polyallomer) and includes a side wall 53 and an end wall 54 which is adapted to be positioned between the distal end of collar 22 and the proximal end of the needle sheath 20 (FIG. 1) for substantially closing the distal end of shield 40. Side wall 53 is shaped as shown so that end cap 52 can be retained on shield 40 by the interlocking mechanical engagement of the side wall 53 and a complementary projection 55 at the distal end of shield 40.

The end wall 54 includes a central needle aperture which is made small enough that the end of shield 40 is closed to the maximum extent while allowing the locking ears 16A of needle hub 16 to be extended through the aperture to permit needles to be mounted and removed while the shield 40 is in its retracted position. The aperture is not, however, large enough to allow the proximal end of the needle sheath 20 to pass through it. The use of the smaller sized needle aperture reduces the likelihood that a child or person with small fingers may accidentally contact the needle point. The end cap 52 also makes the distal end of shield 40 more rigid and resistive to deformation when dropped or otherwise impacted upon a hard surface.

In addition, the rim 54 and its position between the proximal end of needle sheath 20 and the distal end of barrel 10 serves a functional purpose when removing or installing needles on the luer tip 17, for example, in a situation where the filling and injection needles are different. When a needle is to be mounted on the syringe, the syringe is held by shield 40 with the shield 40 in the retracted position. Needle hub 16, which projects from the proximal end of the protective sheath 20, is inserted through the aperture in the end wall 54 and the needle hub 16 is telescoped onto the luer tip 17. Using the conventional cooperative wrenching tabs (not numbered) of the sheath and needle, the needle hub 16 is rotated by twisting and pushing with the sheath to thread the locking tabs 16A within the internal threads 18A in the luer skirt 18 until needle 14 is mounted on the syringe. As hub 16 is threaded onto the luer tip 17, the needle moves axially relative to sheath 20. The shield 40 is prevented from rotating by the abutment of keys 42 against the side surfaces 24C of protrusions 24, while the rim 54 provides a surface against which the needle sheath 20 can be forced. Without this feature, the user could not grasp the shield alone when installing and removing the needle since the force exerted by the needle hub 16 on the syringe luer tip would push the syringe out of the shield. This would mean that the user would have to remember to grasp the barrel 10 and not the shield 40 when removing or attaching the needle 15.

Figure 9:
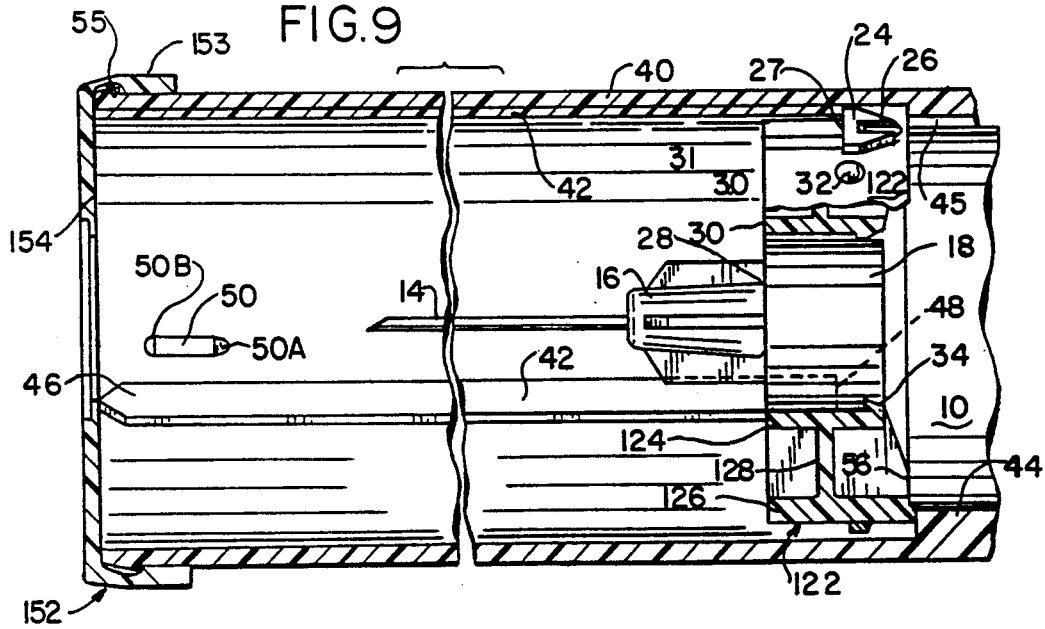
FIG. 9 is a side sectional view showing a collar construction for use with a large diameter barrel.

The end wall 54 is particularly important when the invention is used in conjunction with large diameter syringe barrels. The preferred type of construction for the larger diameter syringe barrels is shown in FIGS. 8 and 9 wherein like numerals are used to identify parts similar to those shown in the embodiment of FIGS. 1–6. In FIGS. 8 and 9 the needle 15 and hub 16 are the same as in FIG. 1 as is the luer tip 17 and the luer lock skirt 18. In this embodiment, however, the collar 122 includes two concentric sleeves 124 and 126 supported by an annular strut 128 forming an I-beam in cross-section as shown in FIG. 9. The end cap 152 includes side wall 153 and end wall 154 which, as shown, covers a substantial portion of the barrel opening and thus greatly reduces the risk of accidental needle stick when the shield is in its extended position.

The device is preferably assembled as follows. Shield 40 is inserted on the distal end of the barrel 10 of an assembled syringe and moved to the retracted position shown in FIG. 1 (with the needle 14 and sheath 20 removed). With the shield 40 held in the retracted position, the collar 22 is placed over the luer lock skirt 18 and inside of the shield 40. As the triangular protrusions 24 on collar 22 contact the triangular points 46 at the end of keys 42 on shield 40, the collar 22 is pushed onto the luer lock skirt 18 causing the shield 40 to rotate until the keys 46 are positioned in the keyways over the detents 32 located between the adjacent triangular protrusions 24. The collar 22 is then pushed inwardly until the proximal end of the collar 22 butts up against the distal face 36 on the syringe barrel. In this position, as shown in FIG. 3, the three detents 50 are seated in the slots 26 of three of the protrusions 24. After the shield 40 and collar 22 have been assembled on the syringe, the end cap 52 is placed on the shield 40. Finally, the needle 14 with its sheath 20 may then be attached to the luer tip 17 to complete the assembly of the present invention.

Alternatively, the collar 22 may initially be positioned within shield 40 with the keys 42 positioned in the appropriate keyways 25. The shield 40 and collar 22 may then be telescoped together over the syringe barrel 10 with the collar 22 being forced onto the luer lock skirt 18 as the shield 40 is moved to the retracted position wherein the proximal end of the collar 22 abuts against the distal face 36 of the syringe barrel 10. Additionally, it is anticipated the alternative assembly method may be used with an open shield wherein the end cap 52 may be placed on the shield after assembly.

The syringe of the present invention may be used in a conventional manner. The needle sheath 20 is removed from the needle 14 and the medication is drawn into barrel 10 by withdrawing the plunger 12 from the distal end of the syringe while the shield is in its retracted position as shown in FIG. 1. After the contents of the syringe have been injected into the patient, the shield 40 is pulled distally into the extended position as shown in FIG. 2. When this happens, the keys 42 slide in the keyways 25 over the spherical detents 32 between the adjacent protrusions 24 on collar 22 (FIG. 4) and the distal surfaces 50A of the detents 50 on the shield 40 slide onto the surfaces 26A of slots 26. The user can feel the end surfaces 48 of keys 42 clearing the spherical detents 32, which signals that the shield 40 is fully extended.

To lock the shield irreversibly in the extended position, the user rotates the shield 40 to cause the keys 42 to move over the adjacent ramp surfaces 28 (or 30) until the keys fall into the locking slots 31 formed between each pair of ramps 28 and 30 (see FIG. 5). Because of the arrangement of the ramps 28 and 30, the shield can be locked by rotating it either clockwise or counterclockwise. When the keys 42 are positioned in the locking slots 31, the proximal edge 48 of each key abuts against the squared off stop surface 27 of one of the triangular protrusions 24 so that the shield 40 cannot be returned to its retracted position without the application of excessive force to the shield 40. Because of the interlocking relationship between the square key 42 and the locking slots 31, the shield 40 can no longer be rotated and, accordingly, the shield is permanently locked in the extended position.

In certain situations, it may be desirable to extend the shield 40 to the position shown in FIG. 2 without locking it in place. For example, if a syringe is to be filled at a location remote from the patient, rather than replacing the sheath 20 after the syringe is filled, it is preferable to extend shield 40 so that it functions as a temporary protective element while the syringe is carried to the patient. The use of the protective shield 40 in this fashion is facilitated by the spherical detents 32 on the collar 22. These spherical detents 32 are positioned in each of the keyways 25 between the triangular protrusions 24 so that when the shield 40 is pulled to its extended position (FIG. 2), the flat end surface 48 of each of the keys 42 abut against one of the spherical detents 32. This prevents the shield 40, when it is in its extended position, from being retracted unless sufficient force is applied to move the keys 42 over the spherical detents 32. Hence, in this situation, the shield 40 is first extended as a temporary sheath for the needle and then returned to its retracted position for administration of the patient's injection. Once the injection has been administered, the shield may again be extended and then locked by rotation so that the shield cannot be retracted. If it is desired to return the shield 40 to its retracted position rather than locking the shield in its extended position, the gradual slope of surface 50B of detent 50 allows the detent to be pushed over the squared off stop surface 27 prior to returning the shield to its fully retracted position.

A further embodiment of the present invention is shown in FIGS. 10 through 18. In this embodiment, an L-shaped trigger member 56 is incorporated on the distal or needle end of the shield 40. The longitudinal portion 58 of the L-shape formed by the trigger member 56 is preferably curved to follow the contours of the shield 40. The trigger member 56 is attached to the shield 40 by a hinge web 60 so that a transverse portion 62 of the L-shape formed by the trigger member 56 extends perpendicularly outward from shield 40. The trigger member 56 is preferably incorporated with the mold of shield 40 and preferably includes a hinge web 60 which is essentially a smaller width extension of the longitudinal portion 58 of the trigger member 56. The material used to make shield 40 is resilient so that the trigger member 56 can be moved following an arc centered around the hinge web 60, without damage, from an initial rest position where the longitudinal portion 58 of the trigger member 56 aligns with the walls of shield 40, to either an inner position or an outer position by rotating the trigger member 56 in an inward or an outward direction, with respect to the shield 40. An inward direction is the direction defined when the longitudinal portion 58 of the trigger member 56 is moved around the hinge web 60 into the interior of the shield 40. An outward direction is defined when the longitudinal portion 58 of trigger member 56 is moved around the hinge web 60 outside of the shield 40. FIG. 11 shows the relative position of the trigger member 56 and shield 40 with the trigger member 56 in the outward position after the latch 70 has released the collar retaining ridge 72.

An end flange 64 projects radially outward around the perimeter of the shield 40 at its distal end. An extension 63 of this end flange 64 projects further from the surface of the shield 40 just below and preferably parallel to the transverse portion 62 of the trigger member 56 in its rest position so that a stop point is established to limit the outward movement of the trigger member 56. A pair of recesses (detents) 66 are disposed along the inside wall of shield 40 across from the hinge web 60. The recesses 66 limit the inward movement of the trigger member 56, as further described below. A pair of locking ears 68 are located at the top of the longitudinal portion 58 of the trigger member 56 and are aligned with the recesses 66. The overall length of the longitudinal portion 58 of trigger member 56, including the locking ears 68, is slightly longer than the inner diameter of the shield 40 measured from the hinge web 60 to the recesses 66. When the longitudinal portion 58 of the trigger member 56 moves inwardly to a horizontal (completely inward) position and extends across the needle end of shield 40, the locking ears 68 of the longitudinal portion 58 engage the recesses 66 on the inner surface of the shield 40. The locking ears 68 and the recesses 66 are shaped so that engagement of the ears 68 with the recesses 66 provides an irreversibly locked arrangement which prevents any outward or further inward movement of the trigger member 56.

The trigger member 56 is locked in an extreme inward position so that the normally open needle end of the shield 40 is covered by the locked longitudinal portion 58 of trigger member 56. This locked portion covers the normally open needle end of the shield 40 to prevent accidental or intentional contact with the needle tip through the open end of the shield. An opening 69 is created in the side of the shield 40 after the longitudinal portion 58 of the trigger member 56 has been moved inwardly to its locked extreme. This opening 69 is then blocked by the transverse portion 62 of the trigger member 56 when it is moved to an axial position and lies within the opening 69 in the shield 40. The now axial transverse portion 62 aligns with the contours of shield 40 and substantially protects and prevents the user from contacting the needle tip through the opening 69 which is temporarily uncovered by the relocated longitudinal portion 58.

When trigger member 56 is in its initial position with the longitudinal portion 58 following the contours of shield 40 and shield 40 is in its fully retracted position as shown in FIG. 10, latch 70 engages with a collar retaining ridge 72 shown in FIG. 13 to prevent movement of the shield 40 with respect to the syringe barrel 10. It is readily anticipated that the trigger member 56 of the present embodiment is readily adaptable for use with any of the preferred shield locking mechanisms described herein and represents an additional means for protecting the open end of the shield.

The shield 40 can be slid to its extended position once the latch 70 is released from engagement with the collar retaining ridge 72. Outward movement by the trigger member 56 disengages the latch 70 from the retaining ridge 72 of the collar 22 and allows the shield 40 to be slid into its extended position, as shown in FIG. 11. Outward movement of the trigger member 58 is achieved by pressing the transverse portion 62 down until it is stopped by the extension 63 of the end flange 64. If the shield 40 is to be kept in its fully extended position after the injection has been given, the trigger member 58 can than be moved inwardly to its extreme inward position so that the locking ears 68 engages the recesses 66, as described above. The syringe 10 can now be discarded in a conventional manner with the contaminated needle fully protected by the locked shield 40 and the locked trigger member 56.

FIG. 12 generally illustrates the preferred form of the shield 40 which may be used individually or with the trigger member 56 wherein the shield 40 may be locked in the extended position and the trigger member 56 will be spaced apart from the distal end of the needle to prevent access to the needle through the open end of the shield 40.

FIGS. 14 through 18 further illustrate the shield locking arrangement located on the collar 22 in accordance with the present invention. Formed onto the surface of the collar 22 are several operational members which are described in detail below. Along the inside wall of the shield 40 lies a key 42, a locking tab 82, and a securing block 76. The key 42 follows a longitudinal path parallel to the needle along the inside wall of the shield and guides the shield 40 as it slides along the collar 22. The key 42 prevents rotation of the shield 40 relative to the syringe barrel 10 (including the collar) until the shield 40 is in its fully extended position. The key 42 slides in a key channel 74 provided in the surface of the collar 22 which is preferably located near the proximal end of the collar 22. A key block 73 lies adjacent to the key channel 74 near the proximal end of the collar 22 and supports the shield 40 as it is slid past the collar 22 and also forms a stop point for the key 42 to prevent proximal movement of the shield 40 when the shield is locked in the extended position as described further below (the term "locked" is used herein with respect to the shield 40 to describe the prevention of further linear or rotational movement between the shield 40 and the collar 22).

In this embodiment, the shield 40 cannot be rotated during its travel to the fully extended position along the collar until the shield 40 has reached the fully extended position due to sliding contact between the key 42 and the key channel 74 of the collar 22. The length of the key 42 is shorter than the length of the shield 40 so that the proximal end of the key exits the key channel 74 only when the shield 40 is fully extended. When this occurs, the shield 40 is no longer guided by the key 42 engagement with the key channel 74 and is free to rotate with respect to the collar 22 and the syringe barrel 10.

A locking recess 78 is located adjacent to the key channel 74 and a ramp 80 and an entry channel 84 are located near the proximal end of the collar 22. The relative positions of the key 42, the locking tab 82 and the securing block 76 along the inside wall of the shield 40 and the positions of the key channel 74, the key block 73 and the locking recess 78 dictate the locking sequence for locking the shield 40 to the collar 22. The locking tab 82 is positioned along the inner wall of the shield 40 so that an inwardly extending projection 83 on the locking tab 82 aligns with the entry channel 84 and will engage the entry channel 84 at the point when the shield 40 is fully extended. The entry channel 84 is shaped so that the engaged inward projection 83, and therefore the shield 40, cannot be extended further. The entry channel 84 does not, however, prevent the inward projection 83 and the shield 40 from returning to the retracted direction (re-exposing the needle) while the locking tab 82 is positioned in the entry channel 84 (FIG. 15). The entry channel 84 is preferably wider than the width of the locking tab 82 as measured circumferentially along the collar 22 and the shield 40, respectively.

To irreversibly lock the shield 40 in its extended position, the shield is rotated counter-clockwise until the inward projection 83 of the locking tab 82 leaves the entry channel 84, travels up the inclined ramp 80 and drops into the locking recess 78. At this point, the end of the key has become misaligned with the key channel 74 and is now positioned adjacent to the distal side of the key block 73 and the securing block 76 is positioned adjacent to the proximal side of the key block 73 to prevent longitudinal movement of the shield 40 about the collar 22. The shield, which must be rotated clockwise to realign the key with the key channel 74 in order for it to be retracted, is prevented from any rotation due to the inward projection 83 of the locking tab 82 being securely engaged in the locking recess 78. The shield 40 is now locked in its extended position and cannot be returned to the retracted position without applying excessive force to the shield 40.

In FIG. 15, a key alignment taper 88 and a locking tab insertion ramp 90 are illustrated along the lower edge of the collar 22 to assist in the assembly of the present invention by aligning the key into the key channel 74 and to Q initially insert the locking tab 82 over the collar 22 and into the entry channel 84. As described above, the securing block 76 is oriented above and slightly offset from the end of the key 42. The securing block 76 operates in combination with the locking tab 82 to prevent the shield 40 from being removed from the collar 22 when the shield 40 has been rotated into the locked position. When the shield 40 is rotated to the locked position, rotation of the shield about the barrel will move the locking tab 82 into the locking recess 78 and, simultaneously move the securing block 76 counter clockwise against the key block 73 on its proximal side so that the key block 73 interferes with the securing block 76.

A further embodiment of the present invention is shown in FIGS. 19-21. A key block 100 is fixed to either a collar which is attached to the distal end of the syringe barrel 10 or to the syringe barrel directly (shown in phantom in FIG. 19). A key block channel 102 is disposed along the inside wall of the shield 104 and accepts the key block 100. The shield 104 can be slid along the syringe barrel 10 and guided by the key block 100 from a retracted position (the needle exposed) to an extended position (the needle protected). A locking channel 106 is provided adjacent to the key block channel 102. The locking channel 106 accepts the key block 100 only when the key block 100 is located in a lockable position, as shown in FIG. 20B. When the key block 100 is in the lockable position, the shield 104 can be rotated so that the key block 100 moves into the locking channel 106. The locking channel 106, as shown in FIG. 20A, preferably begins abruptly at the lockable position defined, in part, by a stop wall 108 against which the key block 100 abuts when it enters the locking channel 106 from the lockable position.

A pair of spring biased stop ramps 110, 112 are positioned in the key block channel 102. Both are formed preferably within the wall of the shield 104 and, are both, spring biased inwardly as shown in FIG. 19. Locking ramp 110 has two inclined surfaces (as shown in FIG. 19), a distal surface 114, and a proximal surface 116, both of which are connected at a single cusp ridge 118 extending inwardly from the wall of the shield 104 and upwardly from the normally flat surface of the key block channel 102. The key block 100 can be slid along either inclined surface 114 or 116 of the locking ramp 110 when the shield 104 is appropriately moved. The stop ramp 112 is positioned adjacent to the locking ramp 110 and provides only one ramp surface (proximal) and a distal edge 120, thereby allowing movement in a single direction with respect to the key block 100 as further described below. The stop ramp 112 is positioned adjacent to the locking ramp 110 so that the key block 100 will be prevented from passing the lockable position as the shield 104 is extended. There exists just enough room for the key block 100 to slide sideways into the locking channel 106 between the stop wall 108 and the distal edge 120 of the stop ramp 112 when the shield 104 is rotated with respect to the syringe.

The proximal surface 116 of the stop ramp 112 is useful primarily during assembly of the present invention to assist in connecting the shield 104 to the barrel of the syringe. The proximal surface 116 of the stop ramp 112 allows the key block 100 to pass the locking ramp 110 during the assembly of the syringe. Otherwise, the locking ramp 110 would act as a one way ramp and resist the passage of the key block 100 over the locking ramp 110 and therefore prevent the shield 104 from passing over the cusp ridge 118. The key block 100 when first inserted, travels along both the proximal surface 116 of the locking ramp 110 and the stop ramp 112, depressing them both. Once past the cusp ridge 118 defined by the transition point of the distal and proximal surfaces, 114 and 116, and also the distal edge 120 of the stop ramp 112, the key block 100 cannot return and the shield 104 cannot be removed from the syringe barrel without the use of excessive force.

If the syringe is being filled and transported prior to use, it may be desirable to temporarily protect the needle, during its transport. To provide such temporary protection, the shield 104 is slid forwardly from its retracted position to its fully extended position. The key block 100 slides proximally in the key block channel 102 to the distal surface 114 of the locking ramp 110 and slightly depresses the distal surface 114 of the locking ramp 110 until the key block 100 contacts the distal edge 120 of the stop ramp 112. At this point the key block 100 and shield 40 are in a lockable extended position and the needle is protected by the surrounding shield 104 which is freely slidable to the retracted position.

If, however, the syringe is to be permanently locked, the shield 104 is rotated about the syringe barrel 10 so that the key block 100 moves from the lockable position to the locked position within the locking channel 106. When the key block 100 enters the locking channel 106

(FIG. 20C), it leaves the distal surface 114 of the locking ramp 110 which, owing to its resilient nature springs upwardly. (towards the barrel). The key block 100 then becomes locked on all four sides, by the side edge of the distal surface 114; the stop wall 108; the shield body 104; and the distal edge of the stop ramp 112. The side edge of the distal surface 114 prevents the key block 100 from re-entering the key block channel 102 and therefore, prevents the shield from returning to its retracted position.

Yet another shield locking arrangement of the present invention is shown in FIGS. 22-25. A collar 140 is provided and attached to the distal end of a syringe barrel 10. The shield 144 includes a channel 146 incorporated along its side wall. The channel 146 is defined by an outer surface 148 and two supporting walls 150. The outer surface 148 is substantially parallel to the surface of the syringe barrel 10. A depressible locking tab 152 is formed in the outer surface 148 of the shield, above the channel 146. The locking tab 152 is secured to the shield 144 by a first hinge web 154. A second hinge web 156 is provided adjacent and parallel to the first hinge web 154 on the proximal end of the locking tab 152. These two hinge webs, 154 and 156, are preferably created when the shield 124 is formed and consist of thinned-out regions of the same resilient material used to make the shield 144. The locking tab 152 includes a locking edge 153 which is parallel to the hinge webs (154, 156) and is positioned on the proximal end of the locking tab 152. The locking tab 152 normally follows the contours of the outer surface 148 of the channel 146 until it is pushed into its locked position which is further described below. A rib 151 projects outwardly from the locking tab 152 to provide a leverage point for pushing the tab 152 into its locked position, as shown in FIG. 24.

A guide key 164 extends outwardly from the collar 140 and is attached directly to the distal end of the syringe barrel. The guide key 164 is a block-like projection extending outwardly from the surface of the collar 140 and is shaped so that it can slide longitudinally within the channel 146 without excessive radial movement while controlling the sliding movement of the shield along the syringe barrel. The guide key 164 includes a locking flange 166 along its distal (closest to the needle) upper edge. The locking flange 166 lies parallel to and inwardly from the inner surface of the channel 146 to define a locking space 168 between the collar 140 and the underside (side closest to the collar) of the projecting locking flange 166, adjacent to the distal surface of the guide key 164 (FIG. 24).

Disposed within the supporting walls 150 of the channel 146 are a pair of opposing retaining hooks 170 which project inwardly towards each other into the channel 146. The hooks 170 are preferably located near the proximal end of the shield 144. When the shield 144 is first positioned onto the syringe barrel, the guide key 164 slides within the channel 146 and past the retaining hooks 170. The hooks 170 are spring biased into the channel 146 and are shaped so that shield 144 can pass the guide key 164 in only one direction, the shield 144 cannot be removed from the syringe barrel after the guide key 164 of the collar 140 is initially slid past the retaining hooks 170. The shield 144 is moveable from a retracted position (needle exposed) to an extended position (needle covered) and will remain in the extended position when it is locked as further described below.

The retaining hooks 170 are positioned along the shield 144 so that when the shield 144 is fully extended, the retaining hooks 170 will contact the proximal surface of the guide key 164 and prevent further extending movement of the shield 144. At this point the shield is in a lockable position.

The locking edge 153 of the locking tab 152 is located above the channel 146 in the shield 144 so that when the shield 144 is in the lockable position the locking edge 153 remains in an overlapping position with respect to the locking flange 166 of the guide key 164.

The locking tab 152 may then be depressed inwardly towards the syringe barrel 10, tearing any frangible points which kept the locking tab 152 aligned with the contours of the shield 144. The proximal overlapping locking edge 153 is supported by the locking flange 166 and directs the inward force against the locking tab 152 distally to bend the locking tab 152 at both hinge web points 154 and 156. The bending of the locking tab 152 at the hinge webs 154 and 156 forces the locking edge 153 to move distally. The locking edge 153 will eventually slide off the locking flange 166 and snap inwardly to contact the inner surface of the locking flange 166 on the collar 140. The resilient nature of the shield material springs the hinge webs proximally to move the locking edge 153 into the locking space 168 to lock the shield 144 in the extended position adjacent to the collar 140.

If the shield is moved proximally, to the retracted position to expose the needle, the locking edge 153 of the locking tab 152 will contact the locking space 168 of the guide key 164 to prevent further proximal movement of the shield about the barrel. Movement to retract the shield will force the distal part of the locking tab 152 inwardly, against the action of the hinge webs 154 and 156, the locking flange 166 will retain the locking edge 153 therein and prevent it from moving from the locked position. The hinge webs 154 and 156 will move the distal part of the locking tab 152 inwardly until contact is made between the surfaces of the collar 140 and the underside of the locking tab 152. The locking tab 152 is illustrated in the lockable position in FIG. 24 and the locked position in FIG. 25.

What is claimed is:

1. In combination,
   (a) a syringe comprising a barrel having distal and proximal ends, a plunger slidable within said barrel, and a needle attached to said distal end of said barrel;
   (b) an elongated needle shield movable over said barrel between a retracted position in which the needle is exposed and an extended position in which said shield surrounds said needle, said shield having an inner surface and including an elongate keyway with an inner surface thereon and an adjacent locking channel along said inner surface;
   (c) a key operatively attached to said distal end of said barrel wherein said key projects radially outward from said barrel to slidably contact said keyway and wherein said locking channel allows entrance of said key therein when said shield is in said extended position, and said extended shield being rotatable with respect to said barrel for moving said key from said keyway into said locking channel; and
   (d) a depressible ramp for preventing movement of said shield about said barrel when said key is in said locking channel and wherein said depressible ramp is movable between first and second positions and said depressible ramp normally extends into said keyway from said inner surface of said keyway in said first position and is depressed from said first position by contact with said key in said second position when said shield is in said extended and rotatable position.

2. The combination of claim 1, wherein said keyway includes at least one longitudinally aligned second ramp structure positioned adjacent said depressible ramp to assist in the alignment of said key into said locking channel.

3. A medical device comprising:
a syringe including a barrel member having distal and proximal ends, a plunger member slightly movable within said barrel member and a needle operatively associated with said distal end of said barrel member, said needle including a distal needle point thereon;
a collar means operatively associated with said distal end of said barrel member, said collar means including a keyway, a first channel member and a key stop thereon, wherein said keyway and said first channel member are oriented laterally offset from each other and said key stop is adapted to extend radially outwardly and circumferentially about said collar means and includes distal and proximal surfaces thereon;
an elongate needle shield having distal and proximal ends and said shield being adapted to be movable over said collar means between a retracted position wherein said needle point is exposed and an extended position wherein said needle point is protected;
an elongate key extending inwardly from said shield wherein said key includes distal and proximal ends and the length of said key is such that when said shield is moved between said retracted and extended positions, said key is aligned in said keyway and when said shield is in said extended position, said key is released from said keyway to enable said proximal end of said key to be misaligned with said keyway and about against said distal surface of said key stop upon rotation of said shield about said barrel member in said extended position;
an inwardly directed tab member on said shield wherein said tab member is adapted to be received in said first channel member when said shield is in said extended position, said tab member being oriented with respect to said key on said shield such that when said tab member is in said first channel member said key is aligned with said keyway and said shield may be returned to said retracted position;
an inwardly directed stop means on said shield wherein said stop means is positioned proximally of said proximal end of said key and is adapted to abut against said proximal surface of said key stop when said shield is in said extended position.

4. The medical device of claim 3 wherein said shield is rotatable about said collar means from a said extended position wherein said shield is movable to said retracted position to a locked and extended position wherein said tab member is received in a locking recess on said collar means.

5. The medical device of claim 4 wherein said key is misaligned with said keyway and said stop means abuts against said proximal surface of said key stop when said tab member is received in said locking recess on said collar means.

6. The medical device of claim 3 wherein said needle includes a needle hub thereon to removably mount said needle on said distal end of said barrel member and an elongate needle sheath is removably mounted on a portion of said needle hub to enclose said needle therein and said shield includes an end wall associated with said distal end thereof and said end wall includes an aperture therein sized to permit passage of said needle hub therethrough while preventing the passage of said needle sheath therethrough.

7. A medical device comprising:
a syringe including a barrel member having a longitudinal axis and distal and proximal ends, a plunger member adapted to be slidably received in said barrel member, and a needle operatively associated with said distal end of said barrel member and said needle including a distal needle point thereon;
an elongated needle shield having an inner surface and distal and proximal ends and wherein said shield is adapted to be movable with respect to said barrel member between a retracted position wherein said distal needle point is exposed and an extended position wherein said distal needle point is protected;
an elongate keyway operatively associated with said inner surface of said shield and said keyway including a proximal end and a locking channel adjacent said proximal end of said keyway;
a key operatively associated with said barrel member wherein said key extends radially outwardly from said longitudinal axis of said barrel member to slidably contact said keyway and wherein said locking channel is oriented with respect to said keyway to receive said key therein as said shield is rotated about said barrel member when said shield is in said extended position;
a depressible ramp member operatively positioned in said keyway wherein said ramp member is positioned adjacent said locking channel and movable between a first position wherein said ramp member extends into said keyway from said inner surface of said shield and a second position wherein said key contacts and depresses said ramp member with respect to said inner surface of said shield.

8. The medical device of claim 7 wherein said ramp member includes a distal surface and a side surface and wherein said key contacts and depresses said distal surface of said ramp member in said second position as said shield is returnable to said retracted position.

9. The medical device of claim 8 wherein said shield is rotatable about said barrel member from said extended position to an extended and locked position wherein said ramp member is in said first position when said shield is in said extended and locked position and in said second position when said shield is in said extended position.

10. The medical device of claim 9 wherein said side surface of said ramp member contacts said key when said shield is in said extended and locked position to retain said key in said locking channel.

11. The medical device of claim 7 wherein said needle includes a needle hub thereon to removably mount said needle on said distal end of said barrel member and an elongate needle sheath is removably mounted on a portion of said needle hub to enclose said needle therein and said shield includes an end wall associated with said distal end thereof and said end wall includes an aperture therein sized to permit passage of said needle hub therethrough while preventing the passage of said needle sheath therethrough.

* * * * *